United States Patent [19]
Bushman

[11] Patent Number: 5,823,207
[45] Date of Patent: Oct. 20, 1998

[54] DENTAL FLOSS APPARATUS WITH IMPROVED MECHANISM FOR COLLECTING SPENT FLOSS AND WITH IMPROVED TIP STRUCTURE, AND METHOD OF USE

[76] Inventor: Rich Bushman, 10975 Stone Bridge Trail North, Stillwater, Minn. 55082

[21] Appl. No.: 598,744

[22] Filed: Feb. 8, 1996

Related U.S. Application Data

[63] Continuation-in-part of Ser. No. 385,461, Feb. 8, 1995, Pat. No. 5,613,508.

[51] Int. Cl.⁶ .................................................. A61C 15/00
[52] U.S. Cl. .......................................... 132/323; 132/325
[58] Field of Search ..................... 132/322, 323, 132/324, 325, 326

[56] References Cited

U.S. PATENT DOCUMENTS

| | | | |
|---|---|---|---|
| 1,166,732 | 1/1916 | Woodhouse | 132/323 |
| 1,454,429 | 5/1923 | Dresser . | |
| 2,376,750 | 5/1945 | Bell | 132/324 |
| 2,735,436 | 2/1956 | Russo | 132/323 |
| 3,734,107 | 5/1973 | Thierman | 132/325 |
| 3,746,017 | 7/1973 | Casselman . | |
| 3,747,612 | 7/1973 | Davis | 132/324 |
| 3,882,879 | 5/1975 | Lucas | 132/326 |
| 3,939,853 | 2/1976 | Spanondis | 132/323 |
| 4,008,728 | 2/1977 | Sanchez | 132/324 |
| 4,151,851 | 5/1979 | Bragg | 132/326 |
| 4,245,658 | 1/1981 | Lecoutrurier . | |
| 4,518,000 | 5/1985 | Leverette . | |
| 4,706,694 | 11/1987 | Lambert . | |
| 4,738,271 | 4/1988 | Bianco . | |
| 4,788,990 | 12/1988 | Wisegerber . | |
| 4,790,336 | 12/1988 | Kuo . | |
| 4,807,651 | 2/1989 | Naydich . | |
| 4,901,742 | 2/1990 | Olson | 132/325 |
| 4,920,992 | 5/1990 | Preciutti . | |
| 4,920,993 | 5/1990 | Mackie . | |
| 4,936,326 | 6/1990 | Eckroat . | |
| 4,941,488 | 7/1990 | Marxer et al. . | |
| 4,942,894 | 7/1990 | Lai . | |
| 4,995,361 | 2/1991 | Lorenzana et al. . | |
| 5,038,806 | 8/1991 | Ewald . | |
| 5,060,681 | 10/1991 | Westbrook et al. . | |
| 5,085,236 | 2/1992 | Odneal et al. . | |
| 5,176,157 | 1/1993 | Mazza . | |
| 5,183,065 | 2/1993 | Mason . | |
| 5,186,191 | 2/1993 | Loubier . | |
| 5,188,133 | 2/1993 | Romanus . | |
| 5,217,031 | 6/1993 | Santoro . | |
| 5,267,579 | 12/1993 | Bushberger . | |
| 5,279,314 | 1/1994 | Poulos et al. . | |
| 5,287,865 | 2/1994 | Fulton . | |
| 5,301,698 | 4/1994 | Ballard . | |
| 5,323,796 | 6/1994 | Urso . | |
| 5,343,883 | 9/1994 | Murayama . | |
| 5,348,032 | 9/1994 | Mason . | |
| 5,433,227 | 7/1995 | Chen | 132/323 |

FOREIGN PATENT DOCUMENTS

| | | | |
|---|---|---|---|
| 654495 | 12/1962 | Canada | 132/324 |

*Primary Examiner*—Cary E. O'Connor
*Attorney, Agent, or Firm*—Patterson & Keough, P.A.

[57] ABSTRACT

The invention is an improved dental floss holder that provides a convenient frame for the flossing of teeth. This dental floss holder allows a user to advance new floss into place ready for use without contact with the floss for improved hygienics and aesthetics. A novel advancing mechanism allows the user to simply advance the floss while holding the handle and moving a knob with a finger. The fresh floss is dispensed from a spool in the handle and the used floss is collected on a separate spool. Both spools are locked during flossing, so the force from flossing does not move the spools. A brake on the dispensing spool ensures that freshly dispensed floss is at the proper tension for use. Alternatively, friction is applied along the path of the floss to supply tension to the floss as it is being dispensed. Broken floss can be easily reattached to the collecting spool. In the preferred embodiment, an empty cartridge containing the dispensing spool can be used to supply an empty collecting spool. An improved tip structure prevents dental floss from inadvertently being removed from the dental floss holder.

24 Claims, 4 Drawing Sheets

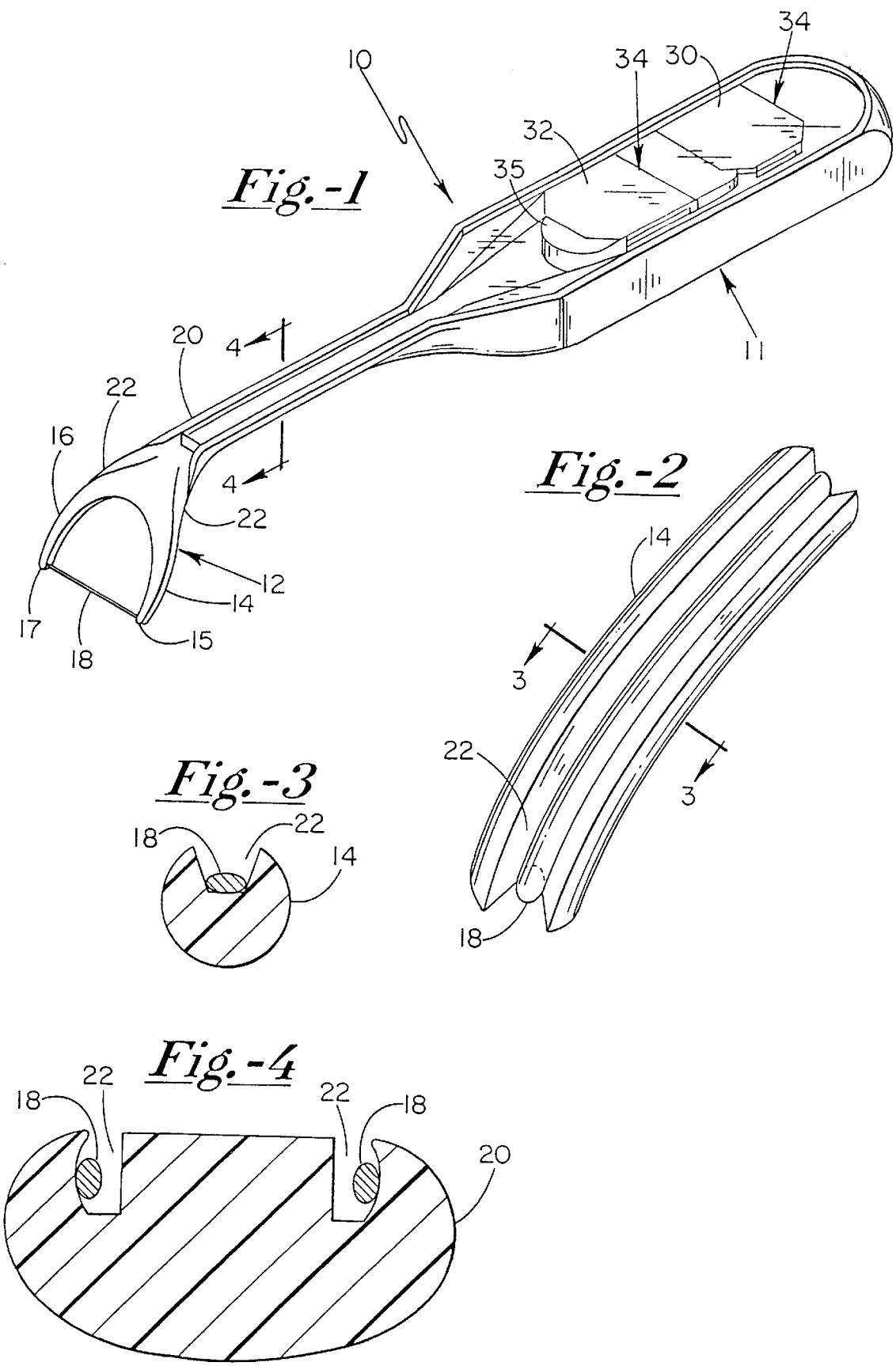

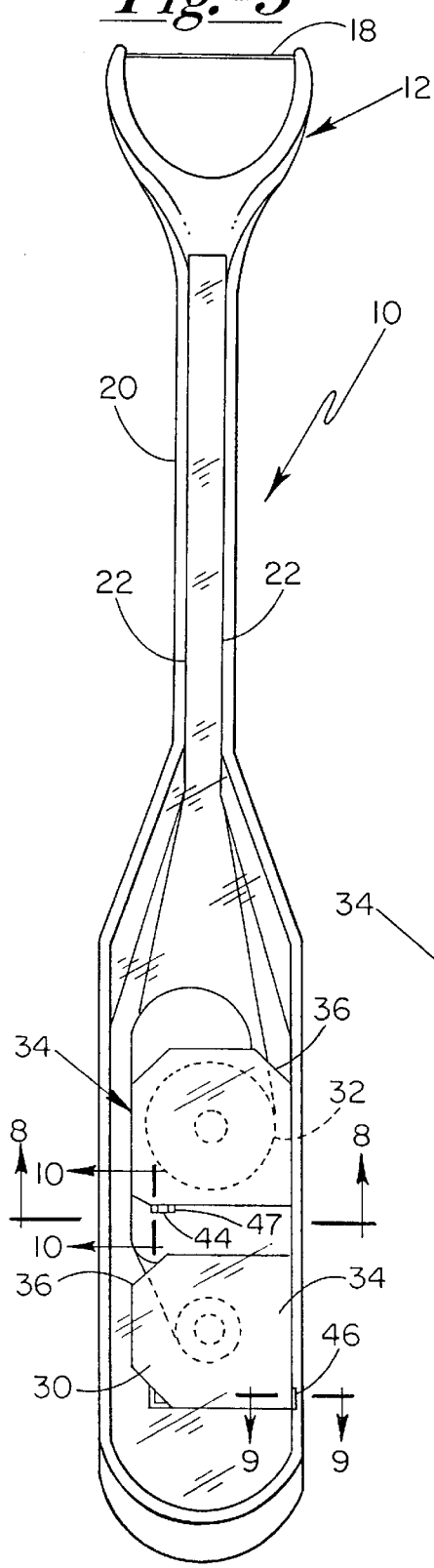
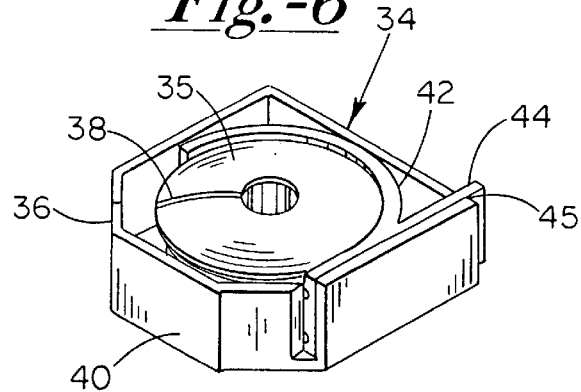
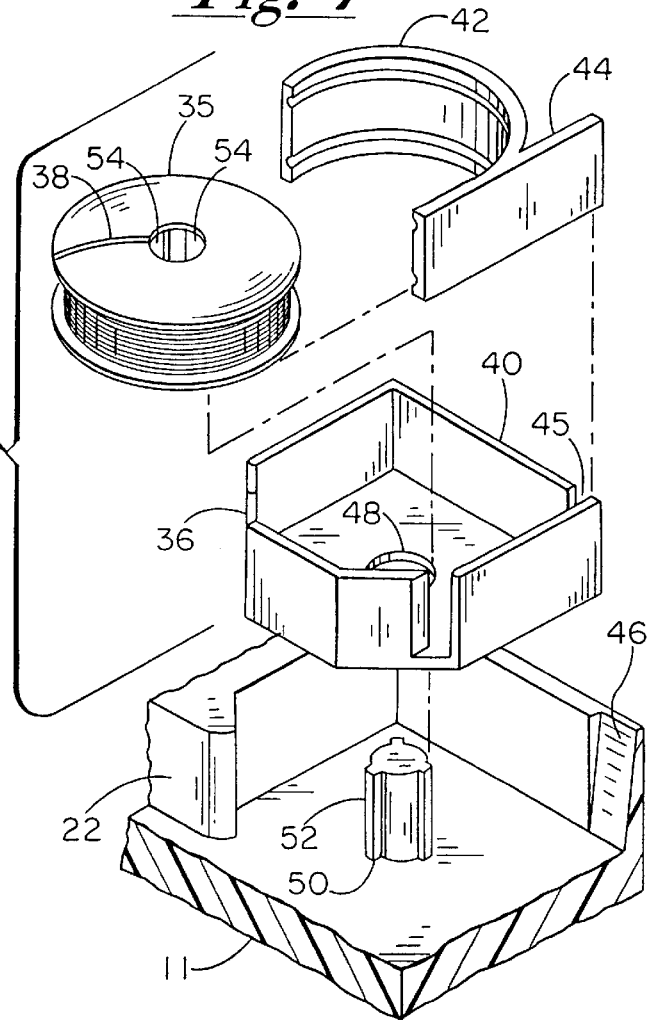

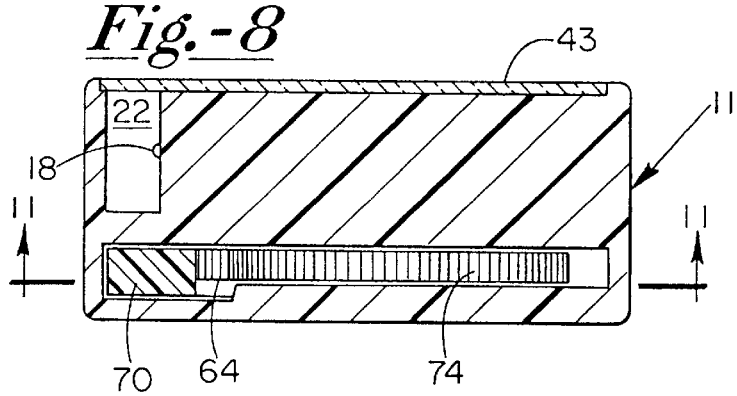
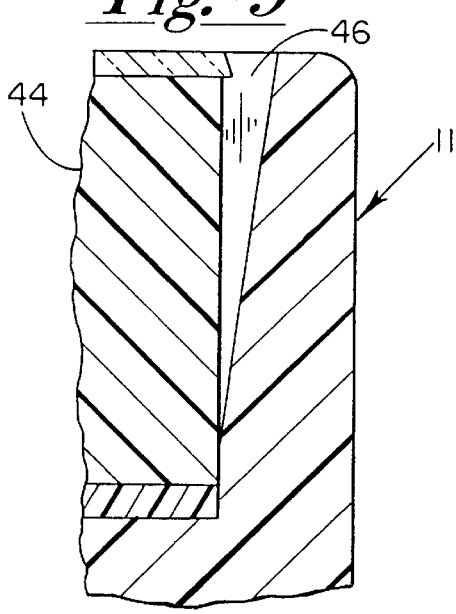
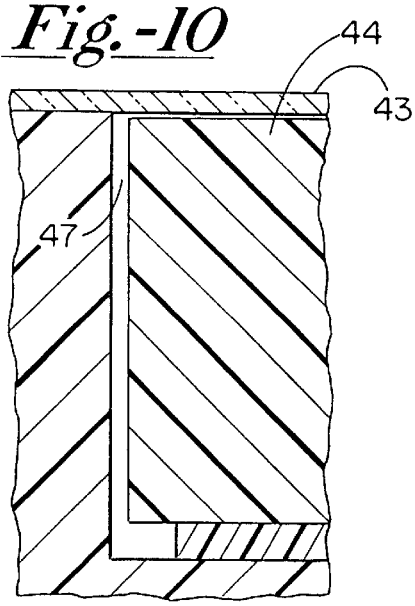
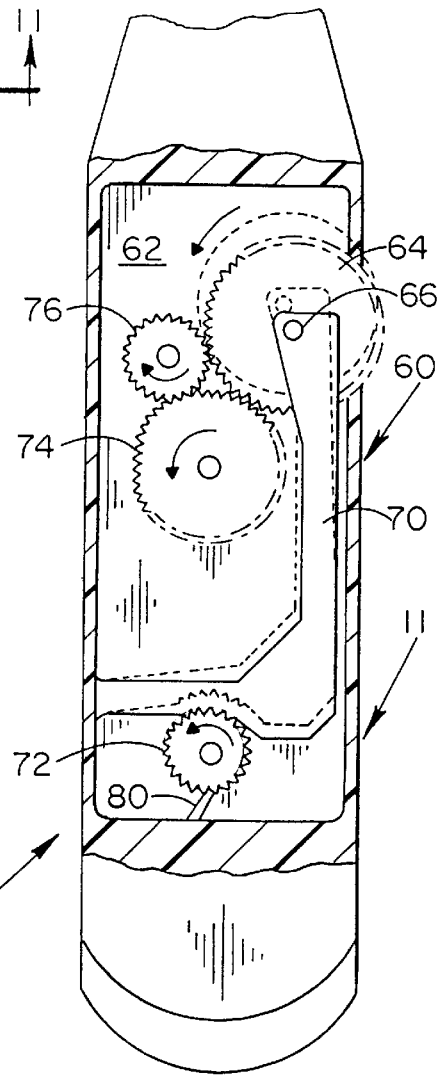
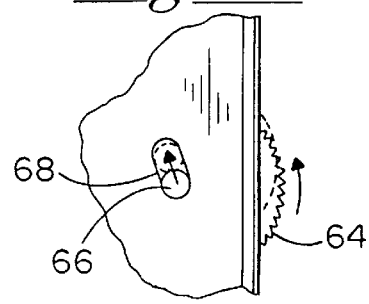

DENTAL FLOSS APPARATUS WITH IMPROVED MECHANISM FOR COLLECTING SPENT FLOSS AND WITH IMPROVED TIP STRUCTURE, AND METHOD OF USE

This application is a continuation-in-part of U.S. application Ser. No. 08/385,461, filed Feb. 8, 1995, now U.S. Pat. No. 5,613,508.

TECHNICAL FIELD

The invention relates to instruments for aiding the flossing of teeth. More particularly, the invention relates to an improved article for holding floss during the flossing process as well as for dispensing clean floss and collecting used floss with minimal user contact with the floss.

BACKGROUND OF THE INVENTION

Tooth flossing is an important part of the regular maintenance of the health of teeth and gums. In its simplest form, floss is dispensed from a container, and each end of a piece of floss is wrapped around a finger on each of the users two hands. The floss is brought into the mouth for use by the motion of both hands. This can be an awkward procedure under the best of circumstances. It is particularly awkward for a person with limited mobility or in circumstances where a person is flossing the teeth of another person such as a dental technician or a person aiding a disabled person or child. Therefore, various attempts have been made to develop implements for simplifying the flossing procedure.

The flossing apparatuses generally have a divergent or fork-shaped head portion with two prongs for holding a piece of dental floss between them. This head portion replaces the fingers that are used in the manual flossing procedure and is the part of the apparatus which is brought into the mouth for doing the actual flossing. The floss must be held relatively taught between the two ends of the prongs to provide a stiff piece of floss for the user to work between their teeth.

The flossing apparatuses also generally have a handle portion which the user can grasp with one hand. While holding the handle, the user can move the forked floss holding end of the apparatus to a proper location for conducting the flossing. There may also be a neck connecting the fork shaped head portion with the handle portion. The neck may make for greater mobility of the apparatus when the fork shaped head portion is inserted in the oral cavity, especially for reaching rear teeth.

While the designs have differed significantly in the shape and orientation of the handle and a fork shaped head portion, an even greater variation exists in the treatment of the dental floss itself in the apparatus. For example, the dental floss can be fixedly attached to the head portion such that the entire head portion must be replaced to refresh the piece of dental floss in position for use. This arrangement is particularly unsatisfactory since the floss may have to be refreshed quite frequently which would make the necessary replacement of the entire head portion both inconvenient and unnecessarily expensive.

Therefore, several designs of flossing apparatuses have contained dispensing spools within the apparatus to supply a source of fresh floss for replenishing the portion of floss in position for use. These apparatuses have a means for cutting off the spent floss once fresh floss has been delivered across the head of the apparatus for use. A tying portion is provided for holding the floss rigidly against the tension produced when using the floss. These designs are not optimal because the spent portion of the floss must be handled by the user for advancing new floss in position for use and for removing the old floss. This is unpleasant when the user is flossing their own teeth, and unhygienic when the user is flossing the teeth of another person. Furthermore, the procedure is time consuming.

To address the problems associated with the disposal of used floss, several designs have incorporated a spool for the specific purpose of taking up the used dental floss. These designs have various degrees of complexity. Several patents have issued for motorized dental floss apparatuses, for example, U.S. Pat. No. 5,176,157, DEVICE FOR SUPPORTING AND OPERATION OF DENTAL FLOSS, U.S. Pat. No. 5,188,133, DENTAL FLOSSING TOOL, and U.S. Pat. No. 5,323,796, AUTOMATED DENTAL FLOSSER. These motorized dental flossing apparatuses have the disadvantage of being relatively expensive and relatively heavy.

Particularly, the U.S. Pat. No. 5,176,157 discloses an apparatus with a dispensing reel and a "truncated cone element" upon which used floss winds around. A motor driven mechanism rotates the truncated cone element and simultaneously rotates a small roller with a swinging motion. The mechanism is designed to run continuously during use to replenish the floss continuously. A dispensing reel is associated with a friction drive means with the amount of friction determined by the screwing or unscrewing of a pawl. It is not clear how the winding up of the floss on the truncated cone element is commensurate with the rotation of the small roller, but it is stated that the floss always remains stretched, even though this would not seem to immediately follow from the design. Periodically, the floss must be cut and removed from the cone element. The main focus of the invention is related to the movement of the floss during use rather than the collection of used floss to minimize handling of the use floss.

A variety of manual dental floss apparatuses with dispensing and collecting spools have been designed. U.S. Pat. No. 4,790,336, DENTAL FLOSS APPLICATOR, describes a device with a supply reel of fresh dental floss and a take-up post. Floss from the supply reel wraps around a reel. Rotation of the reel simultaneously advances floss from the supply reel and rotates the take-up post. Since the amount of floss advanced from the supply reel and the amount of floss collected on the take-up post are not the same amounts, the user must put considerable effort into properly advancing the floss. A floss clip must be used to control the removal of floss from the supply reel. Furthermore, the take-up post is not designed to actually collect a significant quantity of the floss dispensed from the supply reel. Therefore, the clip has a cutting edge for removing much of the floss. Given these limitations in the design of the flossing apparatus of the U.S. Pat. No. 4,790,336, it is not particularly convenient for advancing the floss without handling the used floss, and the user must expend considerable effort to properly advance the floss.

U.S. Pat. No. 5,060,681, DENTAL FLOSSING DEVICE, involves a concentric tapered spool and take-up reel. This device attempts to use the tapered spool to maintain tension in the floss as it is advanced. Since the dispensing spool is tapered, a greater amount of floss is dispensed as more floss is used to account for the greater diameter of the effective collecting spool as floss is collected. For this process to work properly, the floss must unwind and collect perfectly as desired. Also, if any excess floss is introduced, there is no means to take up this excess to allow the device to function with the proper tension again. Perhaps the most serious drawback of this design is that there is no simple way to reattach the floss if it has ripped.

U.S. Pat. No. 5,038,806, DISPOSABLE DENTAL FLOSSER AND HOLDER, describes an apparatus with a spool of unused floss and a take-up reel. The apparatus is designed to approximately dispense and collect like amounts of floss from the respective spool or reel. But the apparatus does not have the means to ensure that the floss remains under tension. Therefore, a guide post is provided for the user to wrap floss around if necessary to increase tension. The spool of unused floss is freely rotatable. This requires an unreasonable amount of interaction by the user to maintain the tension in the apparatus.

Similarly, U.S. Pat. No. 5,301,698, MULTIPLE LOCK DENTAL FLOSS HOLDER AND SPOOL ENCLOSURE ASSEMBLY THEREFOR, discloses concentric dispensing and collecting spools. This apparatus would seem to have no mechanism for adjusting for the different diameters on the dispensing spool and neck upon which the used floss is collected. Therefore, the floss will not remain under tension as the floss is advanced without direct intervention by the user.

Previous designs for dental flossing apparatuses have not provided a mechanism whereby the user can advance the dental floss easily with one hand with a minimum of effort while keeping the floss under sufficient tension to allow flossing. This should be possible with a light, manual apparatus. It should be possible to do inexpensively either with a disposable apparatus or one where the dispensing and collection spools are maintained in cartridges that can be replaced. Such an apparatus would have spools that are locked when the user is not advancing the spool. The apparatus should maintain the tension along the floss while the user is advancing the floss without any effort beyond advancing a knob.

SUMMARY OF THE INVENTION

The advancing mechanism in the flossing apparatus of the present invention locks the dispensing and collecting spools when the user is not advancing the floss. The user moves a knob that causes the collection of used floss onto a collecting spool. The advancing mechanism maintains the tension on the floss while the floss is being advanced, so when the user stops advancing the floss, the floss is at the proper tension for flossing without any further intervention by the user. The flossing apparatus of the present invention preferably has separate cartridges containing the dispensing spool and the collecting spool respectively. The dispensing spool preferably has a curved brake means that engages the dispensing spool to provide generally continuous tension as the floss is dispensed. These cartridges are preferably interchangeable, so the dispensing spool when empty can be put in the place of the collecting spool. The brake in the cartridge would be engaged when the cartridge was used as a dispensing cartridge and not engaged when the cartridge was used as a collection spool.

BRIEF DESCRIPTION OF THE DRAWINGS

FIG. 1 is a perspective view of a dental floss holder within the present invention;

FIG. 2 is an enlarged fragmentary view of one prong of a dental floss support;

FIG. 3 is a sectional view taken along line 3—3 in FIG. 2;

FIG. 4 is a sectional view taken along line 4—4 in FIG. 1;

FIG. 5 is a top plan view of the dental floss holder;

FIG. 6 is a perspective view of a dental floss cartridge removed from the dental floss holder;

FIG. 7 is an exploded view of a dental floss cartridge above a fragmentary view of the handle of the dental floss holder in the vicinity where a dispensing spool cartridge is placed;

FIG. 8 is a sectional view taken along line 8—8 in FIG. 5;

FIG. 9 is a fragmentary, sectional view taken along line 9—9 in FIG. 5;

FIG. 10 is a fragmentary, sectional view taken along line 10—10 in FIG. 5;

FIG. 11 is a cut away, fragmentary, bottom plan view showing the advancing mechanism within the handle of the dental floss holder;

FIG. 12 is a fragmentary, bottom plan view of a portion of the handle of the dental floss holder near the finger wheel;

DETAILED DESCRIPTION OF PREFERRED EMBODIMENTS

Figure 13:
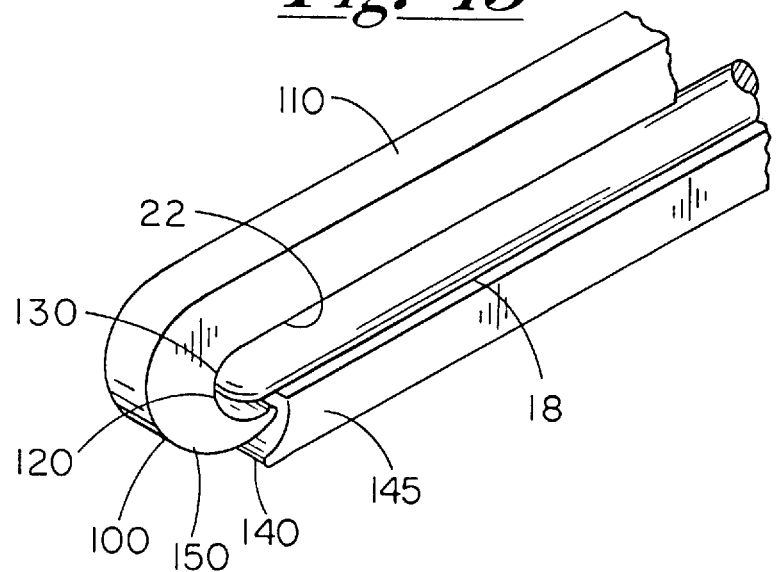
FIG. 13 is an enlarged partial perspective view of one prong of a dental floss support according to the invention.

A dental floss holder 10 of this invention will generally contain a handle 11 and a fork shaped dental floss support 12. The handle 11 is designed to be easily held in one hand by the user. The dental floss support will generally contain two prongs 14, 16 which support dental floss 18 between them during use. The preferred embodiments will have a neck 20 between the handle 11 and the dental floss support 12 to provide improved maneuverability of the floss holder during use. One embodiment (not shown) would allow the reversible folding of the neck relative to the handle to allow for easier transportation with the neck locking in its extended position for use.

Each prong 14, 16 of the dental floss support 12 will have a channel 22 for guiding the floss 18. The channel 22 will direct the dental floss 18 to the tip 15, 17 of the respective prong 14, 16. The tips 15, 17 of prongs 14, 16 can optionally have a hole (not shown) or a notch (not shown) to help hold the floss on the tips 15, 17 during use. The channels 22 continue along the neck 20 to direct the floss 18 toward the handle region 11. The channels 22 can be optionally, partially or completely covered to provide for a more aesthetically pleasing dental floss holder 10. FIGS. 2 and 3 display an exposed channel 22 guiding dental floss 18 along one prong 14, 16. FIG. 4 displays a cross sectional view of neck 20 showing two channels 22.

The handle 11 will contain a dispensing reel 30 and a collecting reel 32. Channels 22 extend to handle 11 thereby directing the dental floss 18 to collecting reel 32 and to dispensing reel 30. In a disposable embodiment (not shown), the dispensing reel 30 and the collecting reel 32 are permanently attached to the handle 11. In this embodiment, when the dispensing reel 30 becomes empty, the user throws away the entire device 10. In a preferred embodiment, the dispensing reel 30 and the collecting reel 32 consist of replaceable cartridges. The use of cartridges allows the replacement of the cartridge when the fresh floss 18 is consumed, so the dental floss holder 10 can be continued to be used, resulting in lower overall costs to the user.

In the simplest case (not shown), a spool itself forms the disposable cartridge with one spool forming the dispensing reel 30 and one spool forming the collecting reel 32. Alternatively, a single cartridge (not shown) can be used to constitute both the dispensing reel 30 and the collecting reel 32. Referring to FIGS. 1 and 5, in a most preferred embodiment, an identical separate cartridge 34 is used for both the dispensing reel 30 and the collecting reel 32. The cartridge 34 is designed such that when dispensing reel 30 is empty, the empty cartridge 34 can be moved into position to take the place of the collecting reel 32. The position of the cartridge 34 on the handle 11 determines whether it is serving as a dispensing reel 30 or a collecting reel 32. The replaceable cartridge 34 is properly used as a dispensing reel 30 when it contains fresh floss and a collecting reel 32 after the fresh floss has been consumed.

Referring to FIG. 6, the replaceable cartridge 34 contains a spool 35. Cartridge 34 has an opening 36 to which dental floss 18 passes when the cartridge is serving either dispensing or collecting purposes. The spool 35 within cartridge 34 has an exposed notch 38 which allows for the reattachment of broken floss when the cartridge 34 is being used as a collecting reel 32. FIG. 7 displays the various components of cartridge 34. The spool 35 sits within a base 40. The spool 35 is held in place by a brake element 42. FIG. 8 displays a cross section of handle 11 between dispensing reel 30 and collecting reel 32 with channel 22 containing dental floss 18. An optional, removable cover 43 covers channel 22 and the top of handle 11 in FIG. 8.

Referring to FIGS. 5–7, the brake 42 has an extension 44 extending through slot 45 which is engaged by the handle 11 at a notch 46 to guarantee that the brake 42 applies tension against the spool 35 when the cartridge 34 is in the position of a dispensing reel 30. When the cartridge 34 is being used to provide a dispensing reel 30, the brake 42 is held against the spool 35 to provide tension during the dispensing of the dental floss 18. Referring to FIG. 9, sloped notch 46 is shown engaging extension 44 of brake 42 thereby applying pressure from brake 42 to spool 35 to create tension during the dispensing of dental floss 18.

In contrast, as displayed in FIG. 5, the brake 42 will not provide a high degree of tension when the cartridge is in a position to provide a collecting reel 32. Referring to FIG. 10, extension 44 is within cavity 47 with sufficient extra space such that there is no force against extension 44. The brake 42 can optionally have a second extension (not shown) to engage the handle 11 to ensure that significant tension will not be applied to the spool 35 by the brake 42 when the cartridge 34 is in a position acting as a collecting reel 32.

As displayed in FIG. 7, the base 40 of cartridge 34 has a hole 48 opening into the center of spool 35. This allows the insertion of shaft 50 through hole 48 into the center spool 35. Shaft 50 has ridges 52 which engage notches 54 in the center of spool 35. Shaft 50 allows for the control of the rotation of spool 35. One shaft 50 is used to engage a spool 35 acting as a dispensing reel 30 and the second shaft 50 is used to engage a spool 35 acting as a collecting reel 32.

Referring to FIG. 11, the advancing mechanism 60 is shown within drive cavity 62 in handle 11 below cartridges 34. Finger wheel 64 protrudes from handle 11 allowing a user to rotate the finger wheel 64. The application of torque to finger wheel 64 moves the finger wheel 64 to a second position shown with phantom lines in FIG. 11. A stub 66 protrudes near the center of finger wheel 64. The stub 66 is constrained to move in groove 68 thereby limiting the range of translation of finger wheel 64, see FIG. 12. Phantom lines in FIG. 12 depict the range of motion of stub 66 and finger wheel 64. Finger wheel 64 is also attached to lever arm 70 which elastically moves with the translation of finger wheel 64 as stub 66 slides within groove 68. The relaxed position of lever arm 70 is shown in FIG. 11 by the solid lines. The flex position of lever arm 70 is shown within phantom lines in FIG. 11.

When lever arm 70 is in its relaxed position, lever arm 70 locks dispensing drive wheel 72 preventing its rotation, and finger wheel 64 locks collecting drive gear 74 preventing its rotation. When lever arm 70 is in its fully flexed position as allowed by stub 66, dispensing drive wheel 72 is free to rotate, and the rotation of finger wheel 64 causes the rotation of intermediate gear 76 which in turn causes the rotation of collecting gear 74. Collecting gear 74 is attached to a shaft 50 such that the rotation of collecting gear 74 causes the rotation of shaft 50 which is in position to be inserted into collecting reel 32. Dispensing wheel 72 is connected to a shaft 50 in a position where shaft 50 will engage dispensing spool 30. Therefore, when lever arm 70 is in its relaxed position the two shafts 50 respectively engaging the dispensing reel 30 and collecting reel 32 are locked in position thereby preventing their rotation. Catch 80 engaging dispensing gear 72 can ensure the dispensing reel 30 may only rotate in one direction, to dispense dental floss 18. A similar catch (not shown) can be used to limit the rotation of collecting gear 74 in one direction.

Finger wheel 64 can be replaced with various notched levers or other structures to perform comparable tasks. These structures that can function in the role of finger wheel 64 are collectively referred to as knobs. The curved brake 42 can be replaced with other mechanisms for providing friction to the spool 35 in the dispensing reel 30. Furthermore, the tension on the floss can be supplied by applying friction to the floss along its path, for example, by having the motion of the floss maneuver around a projection. An appropriate amount of tension can be designed into the floss path. Similarly, the flexing of lever arm 70 can be accomplished through the use of a separate spring (not shown) rather than relying on the natural elastic properties of the material comprising the lever arm 70. Also, different arrangements of gears can be used to transmit the motion of the user's finger to rotation of the collection spool 32.

Even though there are certain advantages to using a manual version, motorized versions of the present invention are possible. Generally, the braking mechanism can be used effectively in motorized versions of a dental floss holder. With respect to the advancing mechanism 60, a motor (not shown) can be used to rotate spool 35 in collecting reel 32. In this case, lever arm 70 can be flexed to unlock dispensing drive wheel 72 by the motion of the switch (not shown) to actuate the motor. Alternatively, the body of the motor can be attached to lever arm 70 whereby the body of the motor will be designed to move in response to rotation of the motor sufficiently to flex the lever arm 70 unlocking the dispensing drive wheel 72.

The preferred embodiment described above describes a particularly simple and convenient method of construction although others can be used. The distinctive features are the locking of reels 30, 32 when the floss 18 is not being advanced and the rotation of collecting reel 30 caused by the motion of the user's finger. The specific relative orientations of the dispensing reel 30 and the collecting reel 32 are not as important so, for example, they can be concentric. An optional cover can be used to cover some or all of various portions of the dental floss holder 10 including the reels 30, 32, neck 20 and portions of the support 12 along with the channel 22.

When a user is flossing their teeth with floss holder 10, they will release finger wheel 64 such that lever arm 70 will be in its relaxed position locking reels 30, 32. Then, dental floss 18 will rigidly span between prongs 14, 16 of dental floss support 12 allowing the user to work the dental floss 18 between their teeth which applies significant tension on the dental floss 18. When the user desires fresh floss in the useable position along the dental floss support 12, the user will rotate finger wheel 64 flexing lever arm 70 thereby unlocking reels 30, 32.

The subsequent rotation of finger wheel 64 induces the rotation of intermediate gear 76 and collecting gear 74. The rotation of collecting gears 74 causes the rotation of collecting reel 32 thereby causing the collection of additional floss 18 on collecting reel 32. As dental floss 18 is wound around collecting reel 32, tension in the dental floss 18 causes the motion of floss within channel 22 as the floss moves down the handle toward the collecting spool, down the neck towards the handle, across the dental floss support 12, up the opposite side of neck 20 and up the handle from the dispensing reel 30. The dispensing reel 30 will dispense fresh floss in response to the tension once any slack in the floss is wound onto the collecting reel 32. The rotation of finger wheel 64 unlocks the rotation of dispensing reel 30, but the force applied by brake 42 restricts the motion of spool 35.

This restriction on the rotation of dispensing reel 30 by brake 42 causes appropriate tension along the entire length of the dental floss from dispensing reel 30 to collecting reel 32. When the user releases finger wheel 64 and lever arm 70 returns to its relaxed position, the tension created during the dispensing of dental floss 18 will result in relatively taught dental floss spanning between prongs 14, 16 of dental floss support 12. This allows the user to immediately use the dental floss holder 10 without performing any other interactions with the device 10 in order to achieve the proper tension along the dental floss 18. In this way, the user can very easily and quickly place fresh floss in a position to be used without handling the used floss. If the dental floss should break, the user can manually advance sufficient floss, thread the floss along channels 22 and reattach the floss to collecting spool 32 by placing the floss within notch 38. Overall, the user's contact with the dental floss is minimized.

Figure 14:
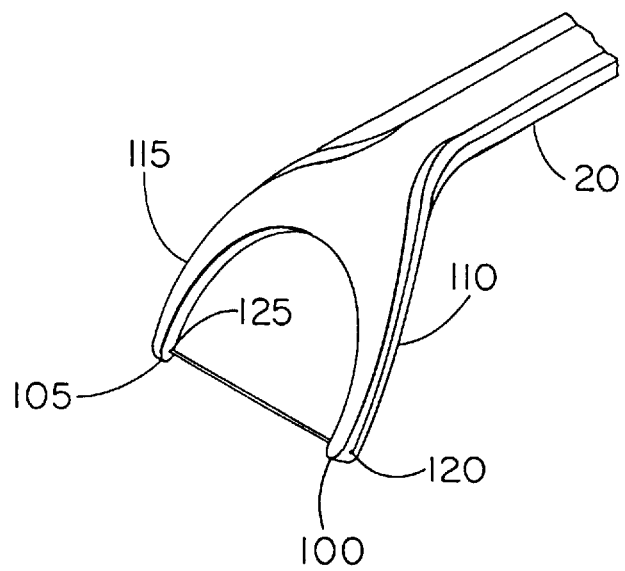
FIG. 14 is a perspective view of a dental floss holder neck and dental floss support.

FIGS. 13–14 illustrate an additional embodiment according to the invention, which is designed to prevent floss from easily escaping from the dental floss holder. The dental floss holder according to this embodiment includes prongs or projections 110, 115 for supporting dental floss 18 between them during use, in a manner similar to the previously described embodiments. Each prong 110, 115 includes guide channel 22 for guiding floss 18 along prongs 110, 115 to tips 100, 105. Guide channel 22 is preferably an open channel, as shown, being open to the outside of the holder. A closed or partially-closed guide channel, however, also could be used.

Tips 100, 105 include structure for preventing floss 18 from being removed inadvertently from prongs 110, 115, as will now be described. Holes 120, 125 in tips 100, 105 allow passage of floss 18 from tip to tip. Holes 120, 125 are of preferably identical construction; therefore to simplify the disclosure only hole 120, on prong 110, will be described with reference to FIGS. 13–14.

As shown in FIG. 13, hole 120 preferably includes a curved inner surface 130 and is of a diameter equal to the width of channel 22. Alternatively, hole 22 could widen out slightly from channel 120, if desired. In either case, the end of tip 100 extends around dental floss 18 to prevent dental floss 18 from escaping hole 120, for example in situations where floss 18 is being pulled in a general direction away from neck 20. In other words, floss 18 is disposed within the hole when the apparatus is in use to prevent inadvertent removal of floss 18 from tip 100.

Tips 100, 105 also include notch 140, which in the illustrated embodiment extends through side wall 145 of prong 110 at hole 120, adjacent guide channel 22. Notch 140 guides floss 18 through tip 100 to and through hole 120. Notch 140 preferably has curved sidewalls to create a generally curved shape, providing tip 100 with a hook-shaped portion 150. Notch 140 is preferably wider at its outside portion than at its inside portion (at channel 22) and, as is clear from FIG. 13, the width of notch 140 decreases along substantially the entire length of notch 140. This differential shape provides relatively easy insertion of floss into the dental floss holder, but makes it relatively difficult to inadvertently remove floss from the holder. The relatively narrow opening of notch 140 bordering channel 22 also reduces the presentation of any sharp or protruding edges to floss 18, minimizing the likelihood of fraying or jamming of floss within the holder.

The design of tips 100, 105 and their respective notches 140 is extremely advantageous, because notches 140 allow floss to be securely fastened within the dental floss holder without likelihood of inadvertent removal. Notches 140 also eliminate the need to thread dental floss 18 through a circular or other shaped small hole before use, which is at best frustrating and may indeed be impossible for those with impaired vision or motor coordination.

Although FIG. 13 illustrates notch 140 as being oriented to guide floss 18 toward neck 20 and the handle of the holder, as the floss moves from the outside of prong 110 toward the inside of prong 110 (i.e. toward the bottom of channel 22), other configurations and positions of notch 140 are also contemplated. For example, notch 140 could be placed on the upper side of prong 110, instead of in lower side wall 145, and/or could be oriented to guide floss away from the handle instead of towards it. Additionally, notch 140 could be of non-curved construction, forming a shape more akin to a trapezoid within side wall 145 (or other wall) than a widening arc. Further, notch 140 could be constructed to have ends of equal dimension.

In one method of loading dental floss into the portion of the holder illustrated in FIGS. 13–14, floss is guided along guide channel 22 and then passed through notch 140 to hole 120. Floss 18 is then directed to notch 140 of the corresponding, opposite prong 115 and passed through the notch to hole 125. The floss is then guided along guide channel 22 defined in prong 115. Of course, other methods of loading the floss are also contemplated; for example, the floss could be passed through the first notch before being guided along the corresponding guide channel, or could be first loaded on projection 115 instead of projection 120.

As is clearly shown in FIG. 13, the diameter of floss 18 is substantially larger than the width of notch 140. As floss 18 slides through notch 140, therefore, it must overcome a friction fit between opposed portions of notch 140 to snap into hole 120. This substantially prevents dental floss from passing back through notch 140 during normal use of the apparatus As is also clearly shown in FIG. 13, the inside edge of notch 140 is disposed at a side of hole 120 nearest the handle. Additionally, a side of hole 120 farthest from the handle is substantially continuous, as shown, and is free of the inside end of notch 140, to substantially prevent inadvertent removal of dental floss 18 from hole 120 through notch 140. Further, also as shown, the inside end of notch 140 is disposed with respect to hole 120 in a direction along dental floss 18 toward the handle. Finally, removing dental floss 18 from the apparatus through notch 140 would require moving floss 18 toward the handle and then away from the handle, to direct it first to the inside end of notch 140 and then along notch 140 toward its outside end.

The embodiments described with reference to FIGS. 13–14 have application to each of the previously described embodiments. For example, the dental floss advancement mechanism described previously can be advantageously used. Various other combinations and modifications will be evident to those of ordinary skill.

We claim:

1. An apparatus for holding, dispensing and collecting dental floss, the apparatus comprising:
   a handle;
   a dental floss support coupled with the handle, the dental floss support comprising a first projection and a second projection with both projections presenting a tip and a dental floss guide channel;
   a dental floss advancement mechanism for advancing dental floss along the guide channels and between the tips of the projections;
   a hole extending through each respective tip to guide dental floss from the tip of the first projection to the tip of the second projection, the dental floss being disposed within the hole when the apparatus is in use to prevent inadvertent removal of floss from the tip; and
   a notch extending through each respective projection at the hole, the notch being constructed to receive dental floss and guide dental floss to and through the hole, wherein a side of the hole farthest from the handle is substantially continuous and is free of an inside end of the notch, to substantially prevent inadvertent removal of dental floss from the hole through the notch.

2. The apparatus of claim 1, wherein the notch is constructed in a curved shape: further wherein the notch has a wider dimension at an outside end of the notch and a narrower dimension at the inside end of the notch at the hole, the width of the notch decreasing along substantially the entire length of the notch.

3. The apparatus of claim 2, wherein the narrower dimension at the inside end of the notch at the hole provides a friction fit between the dental floss and the notch at the inside end of the notch, to substantially prevent dental floss from passing back through the notch during use of the apparatus.

4. The apparatus of claim 3, wherein the inside end of the notch borders the dental floss guide channel and the outside end of the notch is spaced from the dental floss guide channel.

5. The apparatus of claim 1, wherein the inside end of the notch is disposed at a side of the hole nearest the handle.

6. The apparatus of claim 1, wherein each tip includes a hook-shaped portion partially defined by the notch.

7. The apparatus of claim 1, wherein the dental floss advancement mechanism includes:
   a dental floss collecting device;
   a dental floss dispensing device operatively coupled with the dental floss collecting device;
   a mechanism for rotating the collecting device to cause uptake of dental floss, the mechanism for rotating the collecting device also preventing rotation of the collecting device upon release of the mechanism for rotating the collecting device; and
   a mechanism for allowing rotation of the dispensing device upon engagement of the mechanism for rotating the collecting device, the mechanism for allowing rotation of the dispensing device also preventing rotation of the dispensing device upon release of the mechanism for rotating the collecting device.

8. The apparatus of claim 1, wherein the channel is an open channel that is open to the outside of the apparatus.

9. An apparatus for holding, dispensing and collecting dental floss, the apparatus comprising:
   a handle;
   dental floss support means, coupled with the handle, for supporting dental floss, the dental floss support means comprising a first projection and a second projection with both projections presenting a tip and a dental floss guide channel;
   a dental floss advancement mechanism for advancing dental floss along the guide channels and between the tips of the projections;
   hole means, extending through each respective tip, for guiding dental floss from the tip of the first projection to the tip of the second projection, the dental floss being disposed within the hole means when the apparatus is in use to prevent inadvertent removal of floss from the tip; and
   notch means, extending through each respective projection at the hole means, for receiving dental floss and guiding dental floss to and through the hole means, an inside end of the notch means bordering the dental floss guide channel and an outside end of the notch means being spaced from the dental floss guide channel the inside end of the notch means being disposed with respect to the hole means in a direction along the dental floss toward the handle.

10. The apparatus of claim 9, wherein the notch means includes curved sidewalls.

11. The apparatus of claim 9, wherein the notch means includes a wide dimension at the outside end of the notch means and a narrow dimension at the inside end of the notch means, the width of the notch means decreasing along substantially the entire length of the notch means.

12. The apparatus of claim 11, wherein the inside end of the notch means is disposed at a side of the hole means nearest the handle.

13. The apparatus of claim 9, wherein a narrow dimension at the inside end of the notch means at the hole provides a friction fit between the dental floss and the notch means at the inside end of the notch means, to substantially prevent dental floss from passing back through the notch means during use of the apparatus.

14. A method of loading dental floss into at least a portion of an apparatus for holding, dispensing and collecting dental floss, the method comprising:
   (a) guiding dental floss along a guide channel supported by a projection of the apparatus;
   (b) passing the dental floss through a notch disposed in a side of the projection, the notch being adjacent the guide channel and leading to a hole through the projection; and
   (c) passing the dental floss through the hole in the projection; wherein step (b) includes directing the dental floss from an end of the notch at the outside of the projection to an end of the notch at the inside of the projection, the end of the notch at the outside of the projection having a wider dimension than the end of the notch at the inside of the projection; wherein removing the dental floss from the apparatus through the notch requires moving the floss toward the handle.

15. The method of claim 14, further comprising:
(d) after step (c), extending the dental floss across the apparatus to a second projection;
(e) passing the dental floss thorough a notch disposed in a side of the second projection, the notch being adjacent a guide channel of the second projection and leading to a hole thorough the second projection; and
(f) passing the dental floss through the hole in the second projection.

16. The method of claim 15, further comprising:
(g) guiding the dental floss along the guide channel supported by the second projection of the apparatus.

17. The method of claim 14, wherein the end of the notch at the inside of the projection is disposed at the guide channel and the width of the notch decreases along substantially the entire length of the notch.

18. The method of claim 14, wherein step (b) includes directing the dental floss along a curved shape of the notch.

19. The method of claim 14, wherein step (b) includes providing a friction fit between the dental floss and the end of the notch at the inside of the projection, to substantially prevent dental floss from passing back through the notch during use of the apparatus.

20. The method of claim 14, wherein step (b) includes directing the dental floss by the notch to a side of the hole nearest a handle of the apparatus.

21. The method of claim 14, wherein removing the dental floss from the apparatus through the notch further requires moving the floss away from the handle after moving it toward the handle.

22. An apparatus for holding, dispensing and collecting dental floss, the apparatus comprising:
a handle;
a dental floss support coupled with the handle, the dental floss support comprising a first projection and a second projection with both projections presenting a tip and a dental floss guide channel;
a dental floss advancement mechanism for advancing dental floss along the guide channels and between the tips of the projections;
a hole extending through each respective tip to guide dental floss from the tip of the first projection to the tip of the second projection, the dental floss being disposed within the hole when the apparatus is in use to prevent inadvertent removal of floss from the tip; and
a notch extending through each respective projection at the hole, the notch being constructed to receive dental floss and guide dental floss to and through the hole, an inside end of the notch being disposed at a side of the hole nearest the handle.

23. The apparatus of claim 22, wherein the notch has a wider dimension at an outside end of the notch and a narrower dimension at the inside end of the notch at the hole, the width of the notch decreasing along substantially the entire length of the notch.

24. An apparatus for holding, dispensing and collecting dental floss, the apparatus comprising:
a handle;
dental floss support means, coupled with the handle, for supporting dental floss, the dental floss support means comprising a first projection and a second projection with both projections presenting a tip and a dental floss guide channel;
a dental floss advancement mechanism for advancing dental floss along the guide channels and between the tips of the projections;
hole means, extending through each respective tip, for guiding dental floss from the tip of the first projection to the tip of the second projection, the dental floss being disposed within the hole means when the apparatus is in use to prevent inadvertent removal of floss from the tip; and
notch means, extending through each respective projection at the hole means, for receiving dental floss and guiding dental floss to and through the hole means, an inside end of the notch means bordering the dental floss guide channel and an outside end of the notch means being spaced from the dental floss guide channel;
wherein the notch means includes a wide dimension at the outside end of the notch means and a narrow dimension at the inside end of the notch means, the width of the notch means decreasing along substantially the entire length of the notch means;
further wherein the inside end of the notch means is disposed at a side of the hole means nearest the handle.

* * * * *